Figure 1:
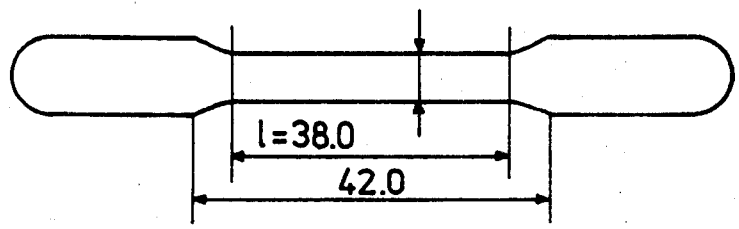

United States Patent [19]

Ducheyne et al.

[11] Patent Number: 4,478,904
[45] Date of Patent: Oct. 23, 1984

[54] METAL FIBER REINFORCED BIOGLASS COMPOSITES

[75] Inventors: Paul L. R. Ducheyne, Blanden, Belgium; Larry L. Hench, Gainesville, Fla.

[73] Assignee: University of Florida, Gainesville, Fla.

[21] Appl. No.: 252,220

[22] Filed: Apr. 8, 1981

[51] Int. Cl.³ .............................................. D04H 1/58
[52] U.S. Cl. ...................................... 428/288; 427/2; 428/289
[58] Field of Search .................... 428/288, 289; 427/2, 427/435

[56] References Cited

U.S. PATENT DOCUMENTS 4,129,680 12/1978 Vines .................................... 428/433
4,159,358 6/1979 Hench .................................. 428/433

OTHER PUBLICATIONS

Donald et al., "Review Ceramic-matrix Composites", Journal of Materials Science, 11 (1976), pp. 949-972.

Primary Examiner—Marion E. McCamish
Attorney, Agent, or Firm—Fleit, Jacobson, Cohn & Price

[57] ABSTRACT

Bioglass for medical and dental implants can be reinforced with metal fibers to improve strength and ductility. The resulting composites may be used as implants without need to be coated on a substrate. A method of producing the same comprises the steps of compacting and sintering an amount of metal fibers followed by impregnating the resulting porous fiber compact with molten bioglass.

13 Claims, 2 Drawing Figures

METAL FIBER REINFORCED BIOGLASS COMPOSITES

This invention relates to metal fiber reinforced bioglass composites and to a method of producing the same. Such composites may be used with advantage in medical and dental implants.

Only a few materials are being used at present for implantation purposes, especially when the implants are subject to high stresses in use. Such materials include stainless steel, cobalt-chromium-molybdenum alloys, cobalt-chromium-nickel alloys, titanium, titanium-aluminium-vanadium alloys, high density polyethylene, dense alumina, and carbon. They distinguish themselves by excellent mechanical propreties and high corrosion resistance but a problem is that these materials tend to cause the formation of a fibrous capsule around them during use and that such capsule will eventually lead to loosening of the implant. Therefore, efforts have been made to develop new materials that are capable of chemically bonding to tissues.

One such new material is formed by surface active bioglass and there is evidence to believe that such bioglass will form a bond with osseous tissue and perhaps with soft tissues under appropriate conditions. A disadvantage of this bioglass material, however, is formed by its limited strength and poor ductility. Therefore, this bioglass has always been used in the form of coatings on either dense alumina or metal. Compare D. C. Greenspan et al, J. Biomed. Mater. Res. Symp. No. 7, 503–509 (1976) for bioglass coatings on dense alumina and U.S. Pat. No. 4,159,358 for bioglass coatings on a metal substrate.

The formation of coatings on alumina or metal is a complicated method, however, and it would be favorable if the bioglass material could be strengthened in such a way that the substrate would no longer be needed.

A major object of the invention therefore is to remove the disadvantages inherent to bioglass materials up till now and to provide a bioglass material that may be used for implants without any need to be coated on dense alumina or metal.

Another object of the invention is to provide a bioglass material having improved mechanical properties.

Still another object of the invention is to provide a method of producing such an improved bioglass material.

A further object of the invention is to provide medical or dental implants consisting of such improved bioglass material.

In accordance with the invention, these objects are met by reinforcing bioglass with metal fibers in order to improve mechanical properties like strength and ductility. The resulting composites may be used as implants without need to be coated on a substrate. They have elastic properties more closely matching the elasticity of the surrounding bone than metallic alloys, thus reducing the risk of bone resorption.

The new metal fiber reinforced bioglass composites may be produced by several methods. Preferably, however, it is produced by compacting and sintering an amount of metal fibers and impregnating the resulting porous fiber compact with molten bioglass. This is an easy and efficient way and leads to a product of excellent quality.

Further objects and characteristics of the invention will be apparent from the following detailed description.

Any suitable bioglass or biologically active glass that is capable of bonding to bone or other living tissue may be employed in the present invention. Suitable bioglasses include those having the following composition by weight:

| | |
|---|---|
| $SiO_2$ | 40–60% |
| $Na_2O$ | 10–32% |
| $CaO$ | 10–32% |
| $P_2O_5$ | 0–12% |
| $CaF_2$ | 0–18% |
| $B_2O_3$ | 0–20% |

These bioglasses have melting points ranging between about 1250° C. and about 1550° C. Especially suitable is a bioglass A which has a nominal composition of 45 weight % $SiO_2$, 24.5% $Na_2O$, 24.5% $CaO$ and 6% $P_2O_5$, and a melting point of around 1350° C.

Further, any suitable type of metal fibers that is compatible with bioglass and that has good mechanical proporties may be used in the present invention. Suitable metals include surgical or dental stainless steel, cobalt-chromium alloys and cobalt-chromium-nickel-molybdenum alloys. The preferred material is stainless steel AISI 316 L which comprises 17–20 weight % Cr, 10–14% Ni, 2–4% Mo and <0.03% C as major alloying constituents.

Metal fibers of any suitable diameter and length may be used, as far as they satisfy the following conditions: the fibers must be capable of forming a coherent mass during compaction, the pores in such a coherent compacted mass must have sufficient dimensions to be filled with glass, and the end product must have sufficient strength and ductility.

For stainless steel fibers, a suitable fiber diameter will range between about 20 and about 200 μm. Both strength and ductility of the end product will be affected when the fiber diameter is below 20 μm or above 200 μm.

There is some correlation between diameter and length of the fibers. Stainless steel fibers of 200 μm diameter and 4 mm length will show insufficient coherence after being compacted to a volume density of 45 vol. %, whereas stainless steel fibers of about 200 μm diameter and about 20 mm length or stainless steel fibers of 100 μm diameter and about 4 mm length will show sufficient coherence after being compacted to the same density.

Further, the length of the fibers will to a certain extent be determined by the geometry of the end product. It will be clear that short fibers having a length of e.g. about 4 mm are preferable for end products of small dimensions such as dental implants whereas longer fibers could be used for end products of larger dimensions provided that they be uniformly distributed about the mass of such products.

The metal fibers should not be cold-worked before use since cold-worked fibers present difficulties during compactation and cannot be sintered without eliminating the strengthening effect of cold working.

The volume ratio between metal fibers and glass will depend from the method used for producing the composite and from the mechanical properties desired therein. In most practical cases, this volume ratio will range between 15% and 70% for stainless steel fibers of 100 μm diameter, and between 20% and 85% for stainless fibers of 200 μm diameter. The lower limit may be smaller than 15% for fibers of 50 μm diameter.

As stated before, any suitable method may in principle be chosen for producing the metal fiber reinforced bioglass composite. However, a preferred method involves impregnating a sintered metal fiber compact with bioglass in molten state. In its simplest form, this method comprises the steps of compacting and sintering an amount of metal fibers and impregnating the sintered compact with molten bioglass. Further, additional steps like oxidizing the fibers at their surfaces after compacting and sintering, a conditioning treatment of the compacted fibers prior to impregnation, and an annealing step after impregnation could be added thereto in some cases to result in a composite of excellent quality.

The compacting step is one of the essential steps in the preferred method, since it determines the shape of the end product and has substantial influence on the volume ratio of metal fibers to bioglass.

This compacting step may be effected by any suitable means, e.g. by placing a weighed amount of metal fibers into a mould and forcing a die into the mould. The pressure of compactation may range between wide limits depending from the fiber material and the desired volume density and may e.g. have any value between 25 and 1000 MN/m$^2$.

The metal fibers may be compacted to any suitable volume density provided that the resulting compact shows sufficient coherence on one hand and sufficient porosity on the other hand. Suitable volume densities may be 45 vol. % or 60 vol. %, depending on the type of metal fibers. The meaning of such values is that 45 vol. % or 60 vol. % of the compact is formed by metal fiber, the rest being air. In general, the volume density may range between 10 and 80 vol. %.

For stainless steel fibers, it has been found that a volume density of 45 vol. % is sufficient for 50 and 100 μm diameter fibers of 4 mm length to render a coherent compact. Such a volume density did not give a coherent compact, however, with fibers of 200 μm diameter and the same length. However, compacts of sufficient coherence could be obtained with all fiber diameters of 50 μm to 200 μm at 4 mm fiber length and a volume density of 60 vol. %.

The sintering step is essential for reaching good results in the preferred method since unsintered compacts of metal fibers will not be filled with glass during impregnation except for a thin surface layer of about 0.1 mm thickness.

Sintering may be effected by transferring the compacted fiber mass to a furnace and heating it therein to sintering temperatures. This may be effected in vacuo or in a reducing atmosphere to prevent undue oxidation.

Any suitable sintering temperature and sintering period may be used but in practice the sintering temperature may range between about 1100° and 1300° C. and the sintering period between about 5 minutes and about 4 hours, dependent from the metal fibers and the volume density of the compacts.

The oxidation step is important to the invented method in order to provide the metal fibers with a surface oxide layer which has excellent bonding properties to bioglass. This step is preferably subsequent to the sintering step and may be effected e.g. by heating the sintered fiber compact in an oxidizing atmosphere.

Any oxidizing atmosphere capable of initiating a chemical reaction with the metal fibers, as well as any oxidizing temperature and period may be used. However, it has been found that subjecting a stainless steel fiber compact to air at about 800° C. for about 20 minutes will result in a sufficiently thick oxidation layer to promote bonding of bioglass to the fiber surfaces. Such oxidation layer will then have a thickness ranging between about 0.5 μm and about 5 μm.

In most cases, the porous metal fiber compact resulting after completion of the compacting, sintering and oxidizing steps will directly be suitable for impregnation with bioglass. Nevertheless, in some cases the porous compact may still be subjected to a special conditioning treatment in order to control thermal expansion and shrinkage of the metal fibers during impregnation.

This conditioning treatment was found to be necessary for compacts of 50 μm diameter stainless steel fibers, since cracks occured in the glass component after impregnation and cooling when this step was omitted.

The conditioning treatment may be effected by maintaining the porous compact at a temperature lower than that of the oxidation step for some time. If the oxidation step is effected at about 800° C., then a suitable conditioning temperature may be around 400° C. The time period should be long enough to effect proper conditioning and may range e.g. from about 10 to about 30 minutes.

Impregnation of the porous metal fiber compact with molten bioglass is an essential step of the invented method. This impregnation can be effected by any suitable means but it is preferred to immerse the porous compact into a bath of molten bioglass and then to withdraw it after a short period.

The quality of impregnation is dependent in first instance from the viscosity of the molten glass, the porosity of the metal fiber compact and the duration of the immersion period. Further, the impregnation quality may be influenced by any pre- and after-treatment of the material.

The viscosity of molten glass is determined by its temperature and composition. For a given glass composition, the glass temperature should be sufficient to keep it in molten state but insufficient to cause volatilization of large portions thereof. A glass temperature of 1350° to 1380° C. is suitable for bioglass of the aforementioned type A and at 1375° C., the viscosity of the bioglass will be sufficient to penetrate most types of porous metal fibers compacts provided that they have sufficient porosity.

The porosity of a metal fiber compact will be dependent from its volume density and fiber diameter and should be sufficient to allow the molten bioglass to penetrate into the pores. Up till now, a minimum porosity limit has not yet been found. Compacts of 50 μm diameter stainless steel fibers having a volume density of 60 vol. % e.g. could still be completely filled with molten bioglass.

The duration of the immersion step should be sufficient to allow the glass to penetrate into the pores of the metal fiber compact but insufficient to allow the metal fibers to reach the temperature of the molten glass. This latter condition is related to thermal expansion and shrinkage of the metal fibers. If there is no time to allow thermal expansion of the fibers during impregnation, their volume shrinkage on cooling will approximately be a shrinkage from the oxidation or conditioning temperature down to normal temperature. Thus, crack formation in the glass will be limited to a minimum.

When using stainless steel fibers and bioglass of type A, a duration of about 3-4 seconds for the immersion step will be suitable. The metal fibers will not reach the molten glass temperature then provided that a 50 μm diameter fiber compact has been subjected before to the above mentioned conditioning pre-treatment.

After impregnation, the resulting metal-glass composite may be cooled to normal temperature. Preferably, however, the composite is first subjected to an annealing treatment of lower temperature than that of the molten glass bath in order to insure relief of excessive stresses in the glass. Such annealing treatment may comprise heating at 400°-550° C. during one to 24 hours and may be followed by slow furnace cooling.

The product of this method is a metal-glass composite which comprises a skeleton of metal fibers embedded in a bioglass matrix and surrounded by a small outer rim of bioglass. This outer rim may have a minimum thickness of about 300 μm and is useful in protecting the metal fibers from reaction with the environment.

The metal-glass composite has improved strength and ductility characteristics in comparison to bioglass itself. For this reason, it can be used in medical and dental implants without any necessity to be coated on a metal or alumina substrate.

The invention will further be illustrated by the following examples which show some preferred embodiments of the invented composites and production methods. Reference will be made thereby to the drawing wherein FIG. 1 is a plan view of a composite specimen as made in the examples and used for testing purposes.

Figure 2:
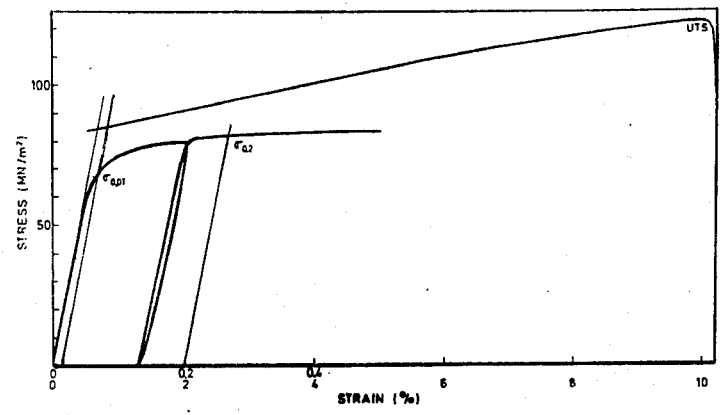

FIG. 2 is a graphical representation of the results of tensile tests effected on composites having 100 μm diameter fibers and a fiber density of 60 vol. %.

EXAMPLE 1

Composites were made from type A bioglass and AISI 316 L stainless steel fibers. The fibers (of 4mm length) had diameters of 50 and 100 and 200 μm and were compacted to different volume densities of 45 and 60 vol. %. For each set of parameters, 7 specimens were made.

The specimens were manufactured as follows: first an amount of fibers suitable for a given geometry (shape and density) was weighed off and was placed in a mould. Then, the fibers in the mould were compacted under pressure to reach a pre-determined volume density. The resulting coherent compact was transferred to a furnace where it was sintered at a temperature of 1250° C. The sintering period was two hours for 50 μm fibers and four hours for 100 and 200 μm fibers. After sintering, the density of the compact was inspected by means of radiography. Then, the surface of the fibers was oxidized by heating the compact for 10 minutes in air at about 800° C. This was followed by a conditioning treatment wherein the compact was maintained and 400° C. for 20 minutes. Thereafter, the compact was immersed for 3-4 seconds into a bath of molten bioglass maintained at 1350°-1380° C. The resulting glass-impregnated compact was annealed at 400°-500° C. for about 4 hours and then slowly cooled in a furnace.

After cooling, the resulting specimens were sand-blasted and ground with a series of silicium carbide grits (up to number 320) in order to remove the excess glass surrounding the composite.

The resulting specimens had the shape of FIG. 1, showing a gauge length of 42 mm and a thickness of 1.8 mm. They could be used as such for tensile and bending tests.

Tensile testing was performed in air with an initial cross-head speed of 0.2 mm/min. At 0.2% yield strength the specimen was unloaded to observe plastic deformation. Thereafter, it was loaded again until fracture at a cross-head speed of 0.5 mm/min. An extensometer with 10 mm span and 10% range was used throughout.

FIG. 2 shows a typical graph recorded from a tensile test of a specimen with 100 μm diameter fibers and 60 vol. % fiber density (indicated as 100-S-60). It is clear that the specimen has a good elastic deformation at first and that this is followed by a plastic deformation up till 10% elongation. In accordance with conventions in metallography, the values of $\sigma_{0.01}$ and $\sigma_{0.2}$ were measured from the graph and used as characteristics for the yield strength of the material. Further, the UTS or ultimate tensile strength for a series of specimens was determined.

The results of the tensile tests are collected in table 1 together with the properties of the porous fiber compacts and those of the parent glass. In this table, a code number 50-S-45 means that 50 μm diameter stainless fibers of 45 vol. % volume density were used. E is the modulus of elasticity and s is the standard deviation. All values are mean values for seven specimens.

TABLE 1

| Sample | $\sigma_{0.01}$ | s | UTS (MPa) | s | E (GPa) | s |
|---|---|---|---|---|---|---|
| Composite 50-S-45 | 59 | 5 | 80 | 17 | 112 | 13 |
| Composite 50-S-60 | 45 | 3 | 81 | 9 | 83 | 4 |
| Composite 100-S-45 | 49 | 12 | 55 | 7 | 98 | 10 |
| Composite 100-S-60 | 55 | 2 | 97 | 11 | 107 | 8 |
| Composite 200-S-60 | 40 | 2 | 54 | 9 | 108 | 18 |
| Steel 50-S-45 | 20 | | 70-110 | | 35 | |
| Steel 50-S-60 | 42 | | 140 | | 65 | |
| Steel 100-S-45 | 10 | | 70 | | 20 | |
| Steel 100-S-60 | 30 | | 135 | | 65 | |
| Bioglass A | | | 42 | | | |

It may be concluded from table 1 that the mechanical properties of the bioglass (in terms of strength and ductility) have been considerably improved by the incorporation of ductile metal fibers therein.

The best results are shown by composites of 50 μm diameter fibers and 45 vol. % fiber density and composites of 100 μm diameter fibers and 60 vol. % fiber density.

Further, 3-point bending tests were performed with the specimens of this example. The specimens had a 3 cm span between supports and a cross-head speed of 0.5 mm/min. The tests were carried out until a bending angle of 90° was reached and the stress required to reach this bending angle was reported. The results are given in table 3.

EXAMPLE 2

Composites were made from type A bioglass and AISI 316 L stainless steel fibers. The fibers had diameters of 50 μm and 100 μm and were compacted to volume densities of 45 vol. % and 60 vol. % respectively. This can be represented by the codes 50-S-45 and 100-S-60.

The composites were manufactured in the same way as in example 1, with the exception that a conditioning treatment for controlling fiber shrinkage was used only for the 50-S-45 specimens.

After cooling, the specimens were sandblasted and then ground with a series of SiC grits of nos. 80, 320 or 600, in order to remove the excess of outward glass.

The resulting specimens had the shape of FIG. 1, showing a gauge length of 42 mm and a thickness of 1.8 mm. They could be used as such for tensile and bending tests.

Tensile testing was performed in the same way as in example 1 and the results are collected in table 2. Each figure for yield strength and ultimate tensile strength is a mean value for 5 specimens.

TABLE 2

| Sample | Surface finish | $\sigma_{0.01}$ (MPa) | s | $\sigma_{0.2}$ (MPa) | s | UTS (MPa) | s |
|---|---|---|---|---|---|---|---|
| 50-S-45 | grit 80 | 57.5 | 10.6 | 79.0 | 13.2 | 94.8 | 20.2 |
|  | grit 320 | 67.1 | 13.6 | 78.6 | 9.4 | 89.6 | 9.6 |
|  | grit 600 | 64.4 | 15.5 | 84.5 | 6.9 | 100.8 | 7.8 |
| 100-S-60 | grit 80 | 55.6 | 10.0 | 72.0 | 5.1 | 95.6 | 13.0 |
|  | grit 320 | 58.3 | 10.7 | 76.2 | 11.3 | 96.2 | 11.4 |
|  | grit 600 | 59.9 | 10.2 | 72.7 | 8.3 | 103.2 | 17.8 |

From table 2, it can be concluded that the metal fiber reinforced bioglass of types 50-S-45 and 100-S-60 has excellent mechanical properties in terms of strength and ductility.

Further, 3-point bending tests were performed in the same way as in example 1. The results are collected in table 3.

The results of the bending tests of examples 1 and 2 are compiled in table 3 together with the combined results of tensile tests from examples 1 and 2. The figures for bending tests are mean values for 10 specimens each, whilst the figures for tensile tests are mean values for 20 specimens each.

TABLE 3

| Sample test | $\sigma_{0.01}$ (MPa) | s | $\sigma_{0.2}$ (MPa) | s | UTS (MPa) | s |
|---|---|---|---|---|---|---|
| 50-S-45 |  |  |  |  |  |  |
| tensile | 61.9 | 11.8 | 78.3 | 11.2 | 91.9 | 15.2 |
| bending | nm* |  | 167.6 | 38.4 | 290.4 | 42.4 |
| 100-S-60 |  |  |  |  |  |  |
| tensile | 57.0 | 8.6 | 73.3 | 7.1 | 97.9 | 12.8 |
| bending | nm* |  | 162.9 | 31.4 | 339.9 | 71.9 |

*nm = not measurable.

The differences in UTS between tensile and bending tests may be attributed to the nature of these tests.

It may be concluded from table 3 that the metal fiber reinforced bioglasses of the present invention have excellent mechanical properties which make them suitable for medical and dental implants without any need to be coated on a substrate.

What we claim is:

1. A metal fiber reinforced bioglass final composite which comprises a compacted, shaped, coherent skeletal mass of metal fibers wholly embedded in a matrix of bioglass, said skeletal mass providing pores throughout and said skeletal mass being sintered so that said pores are filled with the bioglass, the mass occupying a volume of the composite which is in the order of 10–80%, the balance being substantially bioglass.

2. A final composite as defined in claim 1 which is so formed as to provide a dental or medical implant.

3. The method of producing a metal fiber reinforced bioglass composite which comprises the steps of:
   (a) providing metal fibers whose diameters are in the range of about 20 μm to about 200 μm and whose lengths are in the range of about 4 mm to about 20 mm and are so related as to allow a quantity of such fibers to be compacted to a shaped, coherent skeletal mass occupying a volume of the composite which is in the order of 10–80% thereof,
   (b) compacting said quantity of such fibers to form such shaped, coherent skeletal mass,
   (c) heating said shaped, coherent skeletal mass to a sintering temperature in the range of about 1100° C. to about 1300° C. and for a time sufficient to assure subsequent penetration of bioglass into said shaped, coherent skeletal mass,
   (d) immersing the shaped, coherent skeletal mass while at a temperature in the range of about 400° C. to about 800° C. in a bath of molten bioglass which is at a temperature in the range of about 1250° C. to about 1550° C. but for a short time insufficient to allow the skeletal mass to reach said temperature of the bath but sufficient to permit the bioglass to penetrate and fill the voids of the shaped, coherent skeletal mass, and
   (e) recovering the metal fiber reinforced composite from the bath of step (d).

4. The method as defined in claim 3 wherein the temperature of step (c) is 1250° C. and the temperature of molten bioglass in step (d) is 1350° C.–1380° C.

5. The method as defined in claim 4 wherein said metal fibers are stainless steel.

6. The method as defined in claim 5 wherein the diameter of the stainless steel fibers is in the range of about 50 μm to about 200 μm.

7. The method as defined in claim 3 including the step of oxidizing the shaped, skeletal mass at a temperature of about 800° C. for a time sufficient to promote bonding of the bioglass to the fiber surfaces of the shaped, skeletal mass, subsequent to step (c) and prior to step (d).

8. The method as defined in claim 1 including the step of adjusting the temperature of the shaped, coherent skeletal mass to about 400° C. subsequent to the oxidizing step so that the temperature of immersion in step (d) is about 400° C.

9. The method as defined in claim 8 wherein the diameter of the stainless steel fibers is in the range of about 50 μm to about 100 μm 10. The method as defined in claim 9 wherein the volume of the shaped, coherent skeletal mass is about 45% to about 60% of the composite.

11. The method as defined in claim 10 wherein the length of the stainless steel fibers is about 4 mm.

12. The method as defined in claim 11 wherein step (e) comprises annealing the composite at a temperature in the range of about 400° C. to about 500° C. and thereafter slowly cooling it in a furnace.

13. A composite formed by any one of claims 3 or 4–12.

* * * * *